US010606054B2

(12) United States Patent
Gerger et al.

(10) Patent No.: US 10,606,054 B2
(45) Date of Patent: Mar. 31, 2020

(54) SUPER-RESOLUTION FAR-FIELD SCANNING OPTICAL MICROSCOPE (71) Applicant: Sony Corporation, Tokyo (JP)

(72) Inventors: Scott Gerger, Terre Haute, IN (US); Brett Lawson, Terre Haute, IN (US)

(73) Assignee: SONY CORPORATION, Tokyo (JP)

(*) Notice: Subject to any disclaimer, the term of this patent is extended or adjusted under 35 U.S.C. 154(b) by 67 days.

(21) Appl. No.: 15/792,664

(22) Filed: Oct. 24, 2017

(65) Prior Publication Data
US 2019/0018026 A1  Jan. 17, 2019

Related U.S. Application Data (60) Provisional application No. 62/532,420, filed on Jul. 14, 2017.

(51) Int. Cl.
G02B 21/00 (2006.01)
G02B 21/34 (2006.01)
G01N 21/03 (2006.01)
G01N 21/00 (2006.01)

(52) U.S. Cl.
CPC ......... *G02B 21/0036* (2013.01); *G02B 21/34* (2013.01); *B01L 2300/0803* (2013.01); *B01L 2300/0822* (2013.01); *B01L 2300/0887* (2013.01); *B01L 2300/0896* (2013.01); *G01N 21/00* (2013.01); *G01N 2021/0346* (2013.01)

(58) Field of Classification Search
None
See application file for complete search history.

(56) References Cited

U.S. PATENT DOCUMENTS

| 7,141,416 | B2 | 11/2006 | Krutzik | |
|---|---|---|---|---|
| 7,482,577 | B2 | 1/2009 | Gruber | |
| 2002/0001183 | A1 | 1/2002 | Shigehiro | |
| 2004/0226348 | A1 | 11/2004 | Bruce | |
| 2005/0185569 | A1 | 8/2005 | Combs | |
| 2007/0103804 | A1* | 5/2007 | Pang | G02B 21/14 359/894 |
| 2010/0064396 | A1 | 5/2010 | Hidaka | |
| 2018/0250670 | A1* | 9/2018 | Le Berre | G01N 21/01 |

FOREIGN PATENT DOCUMENTS

| KR | 2004 0004014 A | 1/2004 |
|---|---|---|
| WO | WO 02/41004 A2 | 5/2002 |
| WO | WO 02/46721 A1 | 6/2002 |
| WO | WO 2004/065964 A1 | 8/2004 |

* cited by examiner

Primary Examiner — Darryl J Collins
Assistant Examiner — Journey F Sumlar
(74) Attorney, Agent, or Firm — Trellis IP Law Group, PC (57) ABSTRACT A microscope slide comprises a substrate disc characterized by a top surface, and a cover glass characterized by a first surface. The substrate disc comprises a first pattern of nano-structures on the top surface; a second pattern of grooves on the top surface; a third pattern of ridges, characterized by a ridge height, on the top surface; and a fourth pattern of microfluidic guidance features. The cover glass comprises a coating of a metallic alloy with non-linear optical properties on the first surface. The cover glass is bonded to the ridges of the substrate disc to form a sealed chamber between the first surface of the cover glass and the top surface of the substrate disc, such that the ridge height determines a height of the sealed chamber. A method of fabricating such a slide and a method of optical interrogation of a fluid sample are also disclosed.

20 Claims, 6 Drawing Sheets

SUPER-RESOLUTION FAR-FIELD SCANNING OPTICAL MICROSCOPE

CROSS REFERENCES TO RELATED APPLICATIONS

This application claims priority from U.S. Provisional Patent Application Ser. No. 62/532,420, entitled SUPER-RESOLUTION FAR-FIELD SCANNING OPTICAL MICROSCOPE, filed on Jul. 14, 2017, which is hereby incorporated by reference as if set forth in full in this application for all purposes.

BACKGROUND

Optical microscopy-based approaches to the detection and analysis of particles of micron and sub-micron dimensions, suspended or otherwise present within fluid samples, encounter several practical challenges. One is how to provide a clean, sealed environment to contain the fluid of interest. This is typically addressed by placing the fluid either in the well of a microscope slide, under a cover glass, or within immediate contact with the objective lens, scanning probe (e.g. scanning, tunneling, atomic force, near-field) microscopy and the like. Such solutions are limited by a field of view <100 um in diameter and scanning rates typically measured in minutes.

Similar techniques involve a chamber formed into an optical disc, where it can be "read" when the disc is inserted into an optical disc player. Such optical-disc/player based systems in the prior art lack the necessary provisions to reliably focus and track the surface, calibrate the optical system, and to insert, filter, contain, sort, analyze, and dispose of fluids and potential biohazards.

Another challenge to any approach that uses conventional optical systems is that spatial resolution is limited by diffraction effects, to approximately the wavelength of the optical beam. Many particles of interest—for example microvesicles in biological samples—have dimensions well below such "diffraction limits", and so they cannot be observed using conventional optical imaging systems. One alternative is to use more complex scanning systems, that employ a combination of optical and atomic force microscopy. These use AFM probes, micro-cantilevers for example, to in effect create a very small aperture through which near-field imaging is carried out. Such systems require the sample to be positioned extremely close to the optical elements capturing the images, and are relatively complex in operation, as well as expensive. They also share the problem mentioned above of limited field of view and scanning rate limitations.

There remains, therefore, a need for systems and methods that not only provide a clean, sealed environment, necessary for the detection and analysis of fluid samples, but that interrogate the samples using a reasonably simple optical system characterized by a large effective field of view. This may be achieved by an appropriate choice of scanning rate for a sub-micron optical stylus, which could, for example, allow for the formation of a 3-dimensional image approximately 100 mm in diameter within 2 hours. Ideally, the optical system would also provide "super" spatial resolution, significantly smaller than the wavelength of the optical beam, allowing particles with dimensions of a few hundreds or even tens of nanometers to be imaged.

SUMMARY

Embodiments generally relate to systems and methods facilitating the optical detection and analyses of particles present in fluid samples, and more particularly to allowing such detection and analysis to be performed with extremely high resolution.

In one embodiment, a microscope slide comprises a substrate disc characterized by a top surface, and a cover glass, to which the disc is bonded. The substrate disc comprises a first pattern of nano-structures; a second pattern of grooves; and a third pattern of ridges, characterized by a ridge height; all three patterns being present on the top surface. The substrate disc further comprises a fourth pattern of microfluidic guidance features. The cover glass comprises a coating of a metallic alloy with non-linear optical properties on a first surface. The cover glass is bonded to the ridges of the substrate disc to form a sealed chamber between the first surface of the cover glass and the top surface of the substrate disc, such that the ridge height determines a height of the sealed chamber.

In another embodiment, a method of fabricating a microscope slide comprises creating a first pattern of nano-structures, a second pattern of grooves, and a third pattern of ridges into a top surface of a substrate disc; creating a fourth pattern of microfluidic features into the substrate disc; depositing a metallic alloy with non-linear optical properties onto a first surface of a cover glass; and bonding the cover glass to the ridges of the substrate disc to form a sealed chamber between the first surface of the cover glass and the top surface of the substrate disc, such that the ridges determine a height of the sealed chamber.

In yet another embodiment, a method of optical interrogation of a fluid sample present in a chamber within a microscope slide comprising a circular disc bonded to a cover glass comprises operating a dual-beam optical pick-up comprising an imaging beam and a tracking/focusing beam, The operation requires the imaging beam to pass through the cover glass to interact with components of the fluid sample present within a first zone of the chamber, to form one or more images of the components. The operation further requires the tracking/focusing beam to pass through the cover glass to interact with a pattern of grooves present within a second zone of the chamber, radially displaced from the first zone, such that signals are provided that enable stabilization of the imaging beam with respect to at least one of raster scanning in a plane parallel to the disc, and focus in a direction perpendicular to the disc.

A further understanding of the nature and the advantages of the present invention, including embodiments thereof disclosed herein, may be realized by reference to the remaining portions of the specification and to the attached drawings.

DETAILED DESCRIPTION OF EMBODIMENTS

Embodiments described herein enable the expeditious provision of super-resolution images of microscopic particles in a fluid sample, while the sample is contained within a precisely tailored, controlled environment.

The present invention addresses the drawbacks of current alternative approaches to microscopic observation of such particles, offering significant improvements in simplicity and cost as well as in resolution and field of view.

Figure 1:
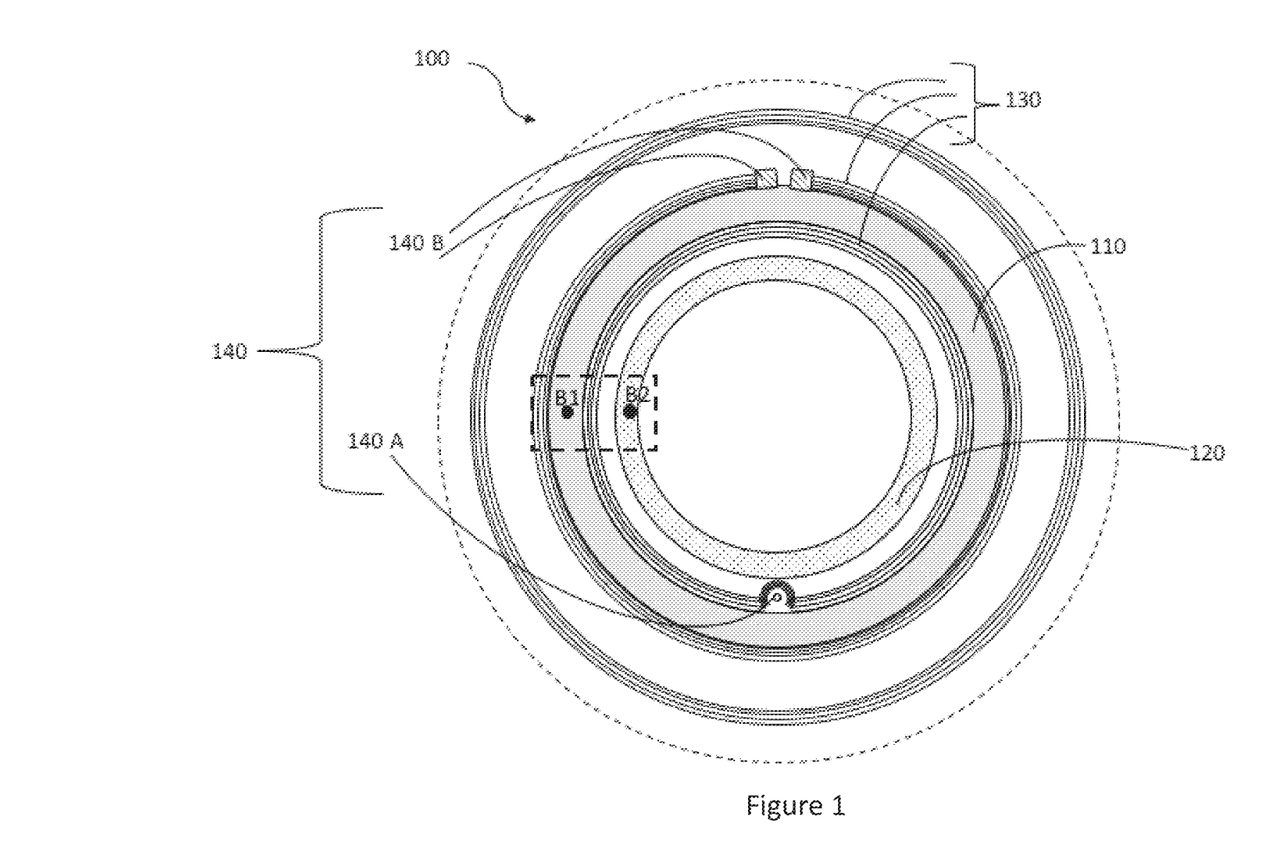
FIG. 1 shows a top-down view of a substrate disc according to some embodiments of the present invention.
Figure 2:
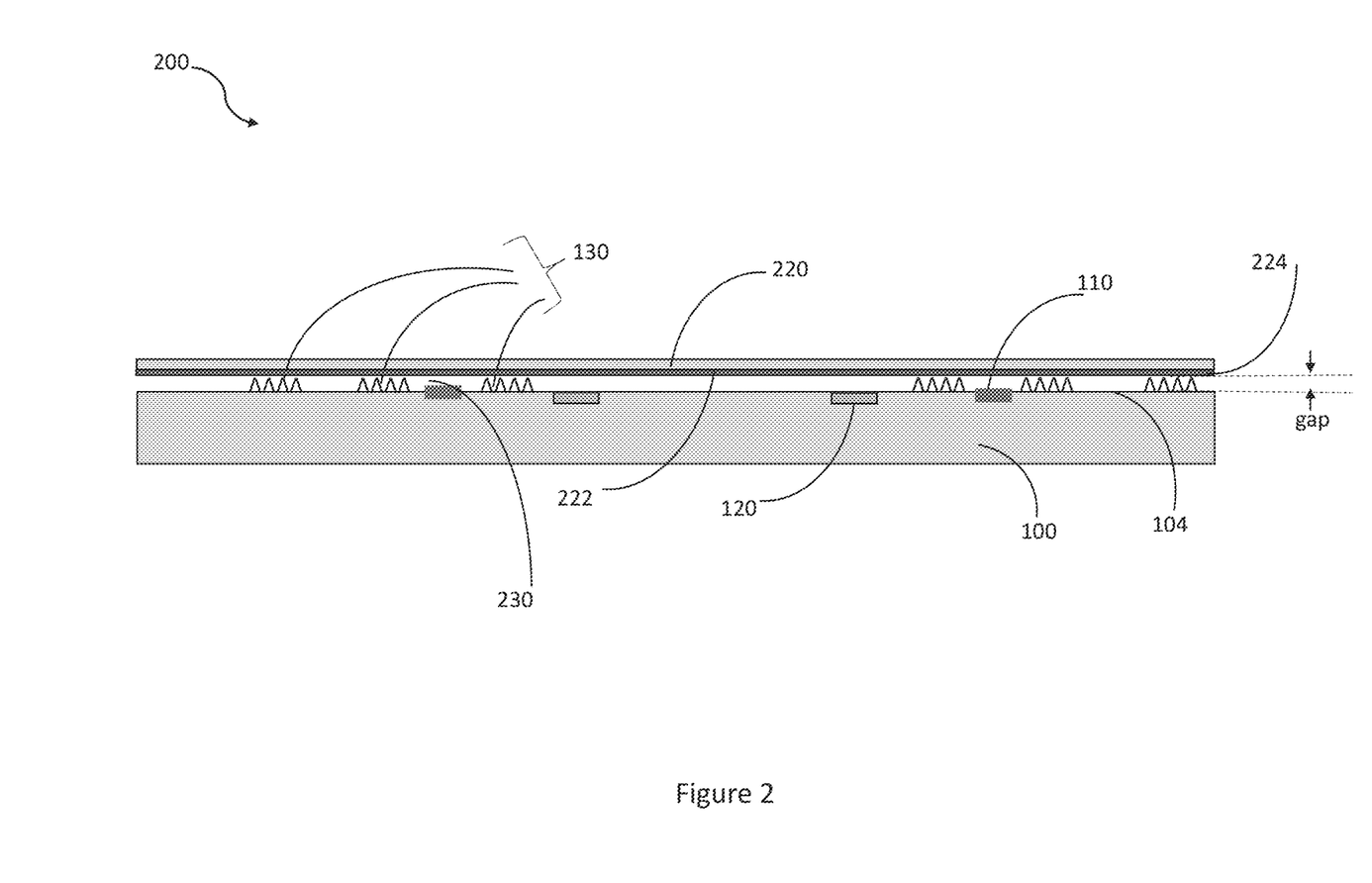
FIG. 2 shows a cross-section view of a microscope slide according to some embodiments of the present invention.

FIG. 1 shows a top-down view of substrate disc 100, while FIG. 2 shows a cross-section view of a microscope slide 200, in which substrate disc 100 is attached to cover glass 220, according to some embodiments of the present invention. The elements in FIG. 1 are seen looking down at top surface 104 of disc 100, while FIG. 2 shows disc 100 with top surface 104 facing upwards, bonded to overlying cover glass 220.

FIGS. 1 and 2 show first pattern 110 of nano-structures, positioned close to second pattern 120 of grooves, both patterns being formed onto or into top surface 104, in annular, concentric zones. Pattern 110 may, for example, be 3-10 millimeters away from pattern 120. The nano-structures may include grooves, pits, ridges, trenches and/or other features oriented radially or tangentially, configured to physically interact with particulate matter in fluids of interest, by, for example, trapping, filtering, sorting, etc., in ways that may lead to identifying the particulate matter, with the aid of an imaging optical beam. In some embodiments aimed at bio-medical applications, the nano-structures include grooves shaped, sized and oriented to enable microvesicles in a fluid sample to be captured.

The grooves of second pattern 120 are configured to allow tracking and focusing adjustments to be made during optical interrogation of the fluid sample. This may be achieved by using a track-and-focus optical beam, operating in conjunction with the imaging optical beam, as part of a dual-beam optical pick-up system, as described below. The second pattern 120 extends circumferentially over disc 100, such that over an angular zone of top surface 104, the pattern 120 comprises a series of concentric arcuate grooves, that over a small area are approximately parallel Second pattern 120 allows stable raster scanning to be achieved in the tangential direction (in the plane of the disc) while maintaining focus in the vertical direction (orthogonal to the plane of the disc). This may be done by aligning and coordinating the imaging beam and the track-and-focus beam, applying well known optical control techniques to the present invention, so that an imaging beam images the particles of interest within an area covered by first pattern 110 while an adjacent track-and-focus-beam tracks reference features in a correspondingly nearby area covered by second pattern 120; optical system adjustments made to stabilize signals provided by the latter beam will correspondingly stabilize the images provided by the former. Example positions of the focused beams on the disc surface are indicated in FIG. 1 by B1 for the imaging beam and B2 for the track-and-focus beam.

FIGS. 1 and 2 also show several sets of ridges on top surface 104, making up third pattern 130. In some embodiments, the ridges follow concentric circumferential paths. The ridges project above top surface 104 of disc 100, as seen in FIG. 2.

Finally, FIG. 1 shows fourth pattern 140 of microfluidic guidance features, closely associated with second pattern 120. Inlet port 140A and outlet ports 140B are shown, but other microfluidic guidance features within the fourth pattern that are not shown explicitly may include channels, chambers, other inlet and outlet ports, reservoirs and gates. The guidance features operate in conjunction with the nano-structures described above to control the passage of fluid into, onto, over, and out of microscope slide 200, before, during and after analysis. In some embodiments, the fourth pattern of microfluidic guidance features is configured to guide the fluid sample along one long spiral path over top surface 104.

Fourth pattern 140 is not shown in FIG. 2 for simplicity, but in general, a cross-section view of a microscope slide of the present invention could reveal indications of one or more microfluidic guidance features.

FIG. 2 also shows cover glass 220, characterized by first surface 224. A coating 222 is present on surface 224. The coating comprises a metallic alloy with non-linear optical properties, operational as explained below. Cover glass 220 is bonded to substrate disc 100 such that the ridges of third pattern 130 act as "stand-offs" or spacers, determining the height of the gap between glass 220 and disc 100. This gap determines the height of one or more chambers 230, formed by the bonding of glass 220 to disc 100, bounded by two sets of ridges of pattern 130, and containing nano-structures of pattern 120. When microscope slide 200 is in use for fluid particulate analysis, chamber(s) 230 will contain the particles of interest, carried thereto by the operation of microfluidic features of pattern 140.

It should be noted that while none of the figures in this disclosure are drawn to scale, the apparent dimensions in the vertical direction of FIG. 2 are particularly exaggerated, for clarity.

In some embodiments, not shown, top surface 104 of substrate disc 100 may include additional features such as a test zone with tracking and focusing features, for use with a reference index fluid and/or particles of known dimensions (e.g. nanometer scale particles) so that reference images may be obtained, to provide normalization. Another option, not shown, is the addition of calibration fields, also on surface 104, to characterize the modulation transfer function of the optical path in situ, specific to each combination of individual microscope slide and optical interrogation system (microscope, Blu-ray player etc). No optical system is perfect and no two optical systems are identical. Therefore it is necessary to provide a means for the system to characterize and calibrate itself in order to provide accurate analyses. Calibration fields may be manufactured into the disc during mastering and include frequency bursts, features of known sizes, shapes, and rates which allow the player to adjust focus and tracking while applying calibration factors to the readback signals in order to normalize any variations among optical elements or disc manufacturing processes. Another option, not explicitly shown, is the inclusion of radially extending features in microfluid features 140, that may allow tests involving centrifugal forces to be carried out. Ordinarily, the disc would be read along helical spiral tracks. The radially aligned-features would be perpendicular to the tracks, allowing centrifugal forces to separate and distribute constituents of the fluid within them, according to their specific gravity or density.

Figure 3:
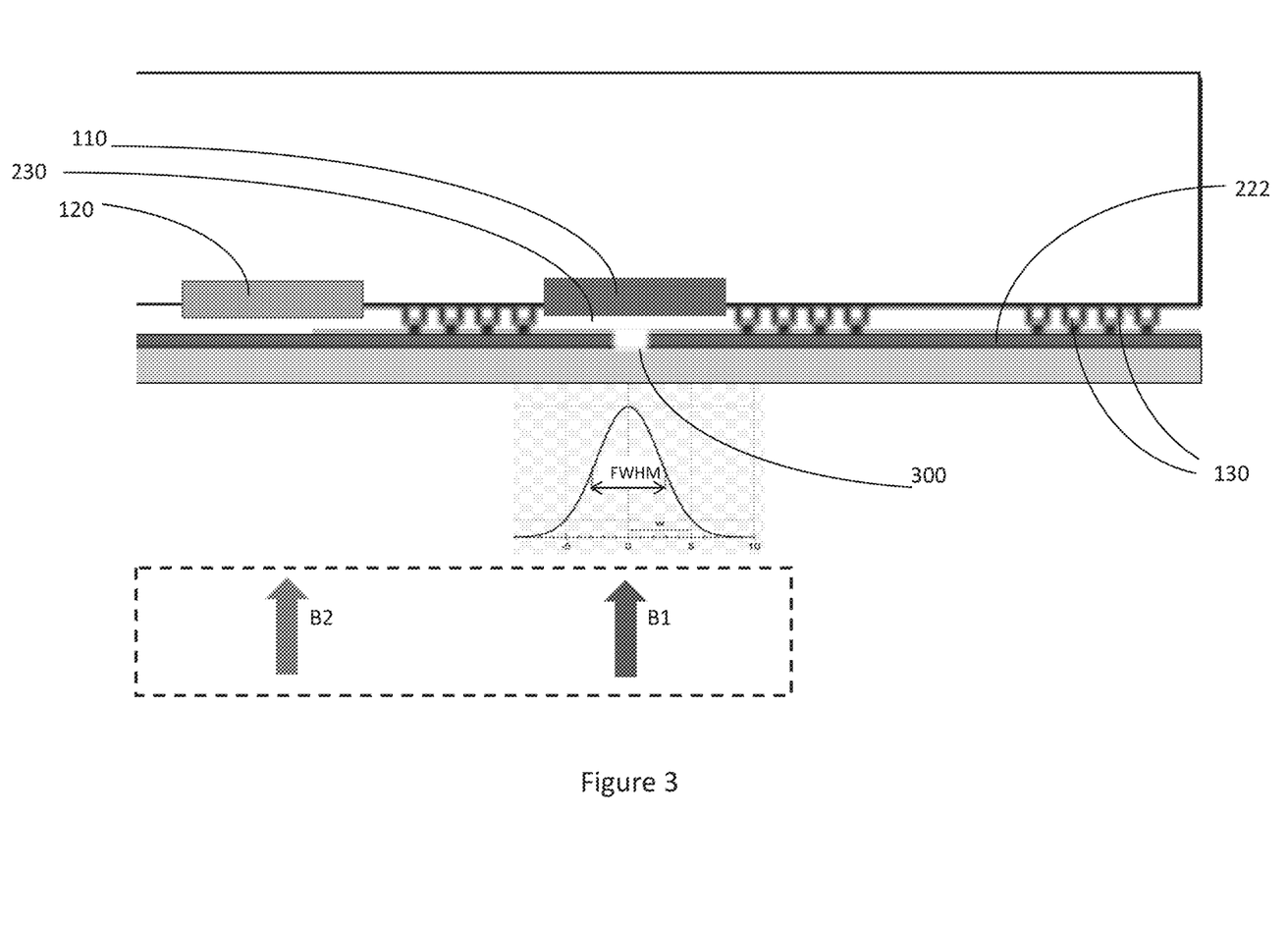
FIG. 3 illustrates the operation of an optical interrogation system according to one embodiment of the present invention, showing the creation of a dynamic aperture.

FIG. 3 shows slide 220 in the reverse orientation to FIG. 2, with cover glass 220 below disc 100, so that material within chamber 230 may be addressed optically from below. This is the typical orientation for an optical disc to be read in an optical disc drive unit. This figure schematically illustrates the formation of a "dynamic pinhole aperture" 300 in cover glass 220 of microscope slide 220 when the slide is interrogated by optical imaging beam B1. The dynamic aperture is formed because the metallic alloy in coating 222 on the first surface of cover glass 220 is chosen to have non-linear optical properties, specifically an extinction coefficient that is substantially reduced when the alloy absorbs radiation at the wavelength and power density of laser beam B1. In some embodiments, the power density of laser beam B2 is also high enough to form a dynamic aperture, not usually necessary for tracking purposes, but possible useful to allow for even higher resolutions to be obtained.

Sb—Te and In—Sb are examples of alloys whose extinction coefficient are substantially reduced by absorption of the laser beam. When this reduction occurs, the material becomes more transparent and less reflective while the reflectivity of the immediately surrounding material is unchanged. A pinhole aperture is therefore created, staying open only where and when the beam is present, so that as the disc spins, the pinhole aperture moves correspondingly, scanning the material of interest. It has been demonstrated that the formation of a dynamic aperture of this sort extends the resolution of an optical system beyond that which would otherwise be possible due to usual diffraction limits.

The effective index and extinction of the material of coating 222 change at the area of high power density (typically <1 mW/μm^2) around the central axis of laser beam B1, enabling the imaging or reading of information over areas (including pits or marks) smaller than would otherwise be expected due to diffraction limits. Resolutions sufficient to image particles as small as 30 nm should be achievable using lasers of wavelength 400 to 410 nm (blue laser diode); 50 nm particle imaging has already been demonstrated.

Figure 4:
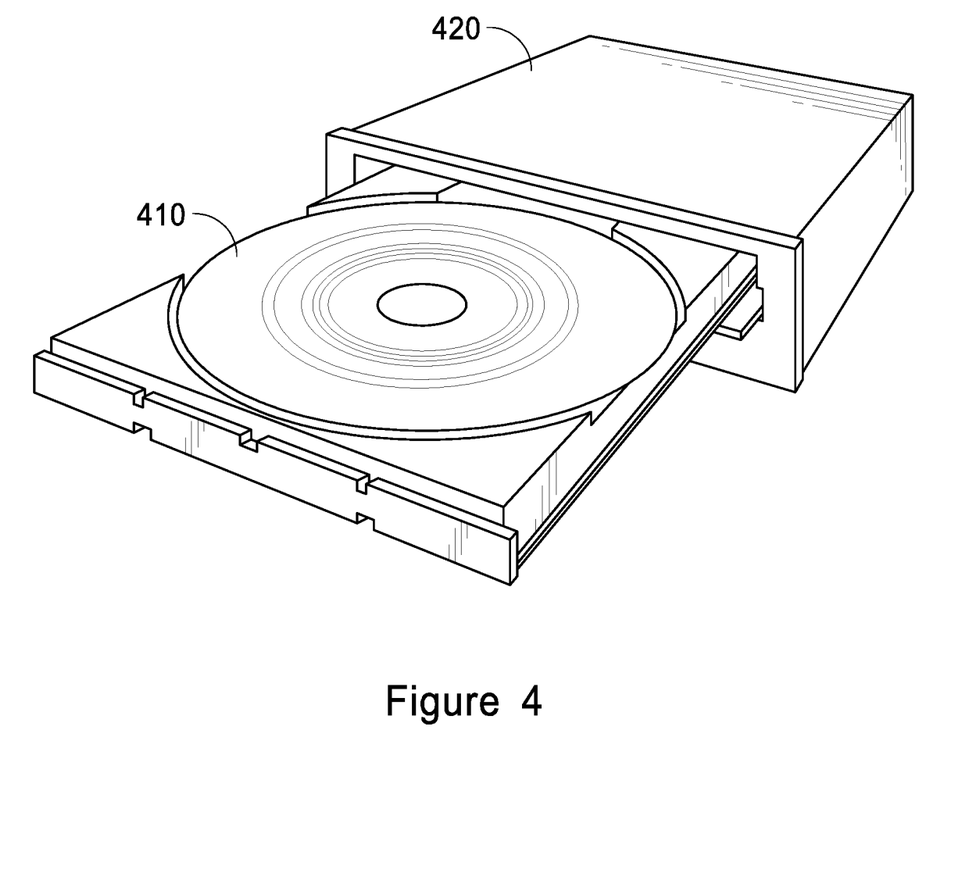
FIG. 4 shows a perspective view of an optical system and microscope slide according to one embodiment of the present invention.

FIG. 4 shows a perspective view of an optical interrogation system 420, either just before or just after reading microscope slide 410, according to one embodiment of the present invention. Optical system 420 is an optical disc drive unit, such as those in common use for reading DVDs, BluRay discs, CDs, magneto-optical discs, or other similar media, that has been slightly modified to incorporate a dual beam addressing system as described above. Such modifications would necessarily include the means for reliable focusing and tracking provided by a parallel set of grooves and navigation patterns such as sector addresses, track numbers, and headers which identify, serialize, and/or authenticate the disc.

Figure 5:
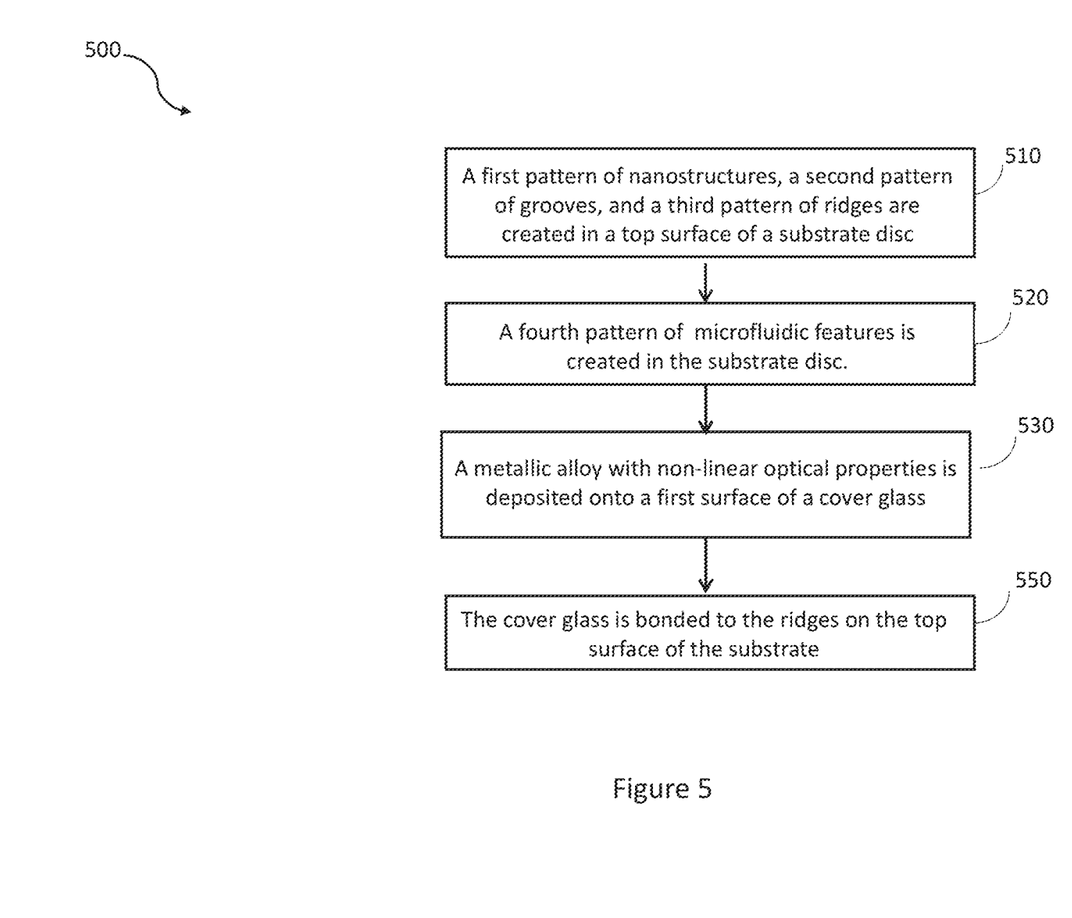
FIG. 5 is a flowchart showing steps of a method of fabricating a microscope slide according to some embodiments of the present invention.

FIG. 5 is a flowchart showing high level steps of a method 500 of fabricating a microscope slide, according to some embodiments of the present invention. At step 510 of method 500, a first pattern of nano-structures, a second pattern of grooves, and a third pattern of ridges are created in top surface of a substrate disc. This step may be carried out using well-known fabrication processes, such as injection molding and stamping, typically used in standard Blu-Ray optical disc mastering techniques. The disc substrate typically comprises a polycarbonate.

At step 520, a fourth pattern of microfluidic features is created in the disc. This formation may be carried out by any one or any combination of well-known fabrication processes, including stamping, molding, electroforming, screen printing, offset printing, ink-jet printing, thermal transfer printing, sputtering, wet or dry etching etc. The features are typically of a few microns in depth, but may be as large as tens of cm in extent over the surface of the disc. In some embodiments, the features include one or more ports for entry and exit of the fluid of interest. These ports, either or both of which could extend through the entire thickness of the disc, may be created during an injection molding process by means of a series of spring-loaded pins installed in the mold.

In some embodiments, the features include a chamber of depth between 1 to 5 microns, shaped and sized to facilitate the flow of the fluid of interest under the constraints of capillary action over the disc surface, to interact with the first pattern of nano-structures described above.

At step 530, a metallic alloy with non-linear optical properties is deposited onto a first surface of a cover glass. At step 540, the cover glass is bonded to the ridges on the top surface of the disc substrate to form the desired microscope slide with all four correctly registered patterns, providing at least one sealed chamber between the first surface of the cover glass and the top surface of the substrate disc, such that the ridges determine a height of the sealed chamber.

Figure 6:
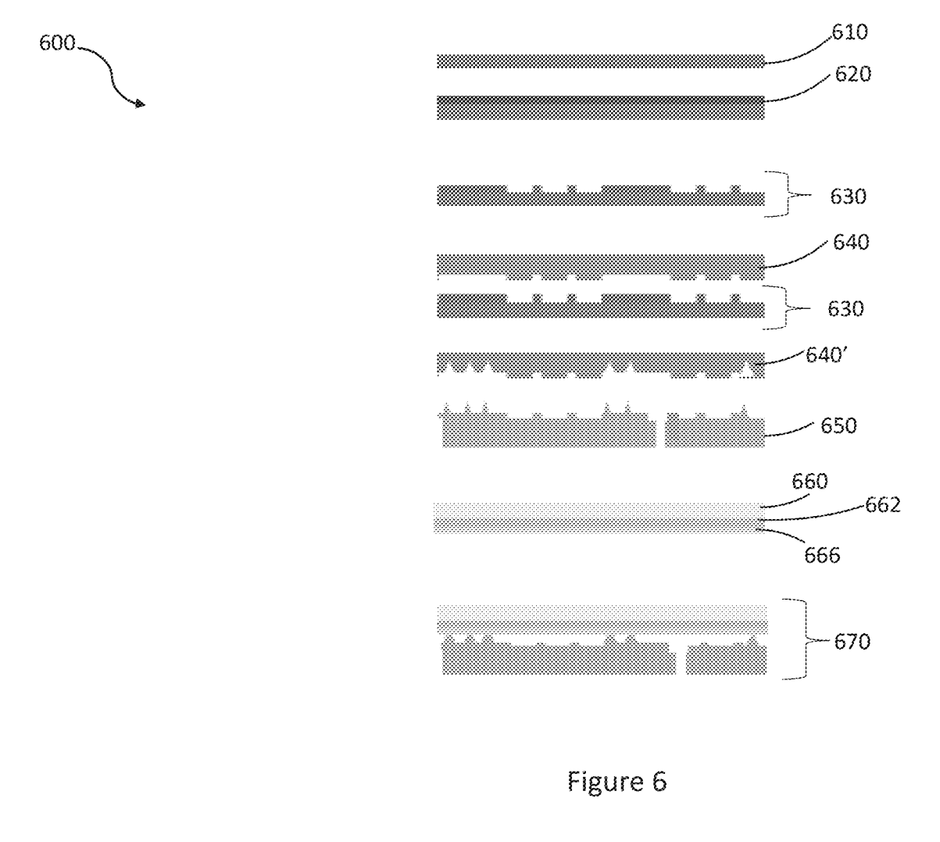
FIG. 6 schematically illustrates steps of a method of fabricating a microscope slide according to one embodiment of the present invention.

FIG. 6 schematically illustrates steps of a method 600 of fabricating a microscope slide according to one embodiment of the present invention, showing cross-sectional views of the main element or elements fabricated at each step.

Method 600 begins at the top of the figure, where a wafer 610 is coated with a photosensitive layer 620, rendering the wafer recordable. A first pattern of nano-structures and a second pattern of grooves are formed into layer 620 by standard recording and developing processes, to create patterned wafer 630. A stamper 640 is created by electroforming from the patterned substrate 630 to provide inverse first and second patterns on one stamper surface, shown facing downwards in the figure. A third pattern of grooves—an inverse of a desired ridge pattern—is formed into that stamper surface, producing fully patterned stamper 640'. In some embodiments, this step is carried out using a laser beam to cut the grooves into the stamper.

Stamper 640' is then operated to transfer the desired first, second and third patterns into a first surface, shown facing upwards in the figure, of a substrate disc. Either before, during, or after the stamping process, a fourth pattern of microfluidic guidance features is created in the substrate disc, resulting in fully patterned disc 650, having four patterns, mutually registered as desired.

The steps of method 600 leading to disc 650 as just described may be considered to make up a detailed implementation of steps 510 and 520 of method 500, discussed above with respect to FIG. 5.

Returning to FIG. 6, either before, during or after the formation of disc 650, a metallic alloy with non-linear optical properties is deposited onto a first surface of a cover glass 660. This is typically achieved by sputtering a film 662 of the alloy onto the glass. Next, a layer 664 of a bonding agent such as a UV-curable resin is deposited on top of film 662. This may be done by spin coating, and typically follows a preliminary step of thorough cleaning and application of an adhesion-promoting primer such as HMDS.

Finally, the coated cover glass 660/662/664 is bonded to the ridges of the substrate disc under UV light, registering the disc and glass properly to form the desired microscope slide 670, including at least one sealed chamber, whose height is determined by the height of the ridges of the third pattern. The resin seals prevent contamination and loss of the fluids of interest when the slide is used for its intended analytic purpose.

Embodiments of the present invention may be developed for applications beyond the bio-medical field, as the contents of almost any fluid may be analyzed, using an appropriate choice of microfluidic features from a nearly infinite design choice of channels, chambers, reservoirs, gates, ports etc. In a similar way, the exact design of nano-structures in the disc substrate may be tailored to sort and filter particles or precipitates in the study of chemical fluid reactions. In some cases, reagents may be pre-injected into microfluidic features such as the channel into which the fluid of interest will be drawn. Binding with these reagents to form optically detectable products could enable highly sensitive chemical or biological analysis of any of a variety of fluid parameters—pH, conductivity, concentration of a dissolved material of interest, presence of a drug or hormone or steroid of interest, etc. Opto-acoustic applications may also be envisaged, where the microfluidic features include acoustic waveguides and related elements allowing highly sensitive analysis of non-compressible fluids to be performed. Excitation of the fluid by sonic, sub-sonic, and/or ultrasonic waves will alter the reflected beam, causing a measurable change in the resulting electronic signal(s). Acousto-Optic modulators are examples of this effect and are used widely in optical communications and data storage contexts.

Embodiments described herein provide various benefits. In particular, embodiments enable a user to quickly and conveniently detect and analyze sub-optical wavelength particles within small volumes of fluid, in a clean environment, which is particularly advantageous in biological and bio-medical fields. The analysis may be performed using slightly modified, widely available optical disc drive units, and can provide extremely high accuracy and precision.

Although the description has been described with respect to particular embodiments thereof, these particular embodiments are merely illustrative, and not restrictive.

In some particular embodiments, multiple steps shown as sequential in this specification can be performed at the same time. It will also be appreciated that one or more of the elements depicted in the drawings/figures can also be implemented in a more separated or integrated manner, or even removed or rendered as inoperable in certain cases, as is useful in accordance with a particular application.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A microscope slide comprising:
   a substrate disc characterized by a top surface, the substrate disc comprising:
   a first pattern of nano-structures, having dimensions between 0.1 nm and 100 nm, on the top surface;
   a second pattern of grooves on the top surface;
   a third pattern of ridges, characterized by a ridge height, on the top surface; and
   a fourth pattern of microfluidic guidance features; and
   a cover glass characterized by a first surface, the cover glass comprising:
   a coating of a metallic alloy with non-linear optical properties on the first surface;
   wherein the cover glass is bonded to the ridges of the substrate disc to form a sealed chamber between the first surface of the cover glass and the top surface of the substrate disc, such that the ridge height determines a height of the sealed chamber.

2. The microscope slide of claim 1 wherein the first pattern of nano-structures is configured to interact with a fluid sample such that particles of interest in the sample are contained, guided, and/or otherwise positioned within the chamber to allow for optical interrogation using a microscope.

3. The microscope slide of claim 2 wherein the fourth pattern of microfluidic guidance features is configured to guide the fluid sample along a spiral path over the top surface, within the sealed chamber.

4. The microscope slide of claim 2 wherein the fourth pattern of microfluidic features is configured to provide entry of the fluid sample into the first pattern of nano-structures from an external source.

5. The microscope slide of claim 4 wherein the fourth pattern of microfluidic features is further configured to provide exit of a portion of the fluid sample out of the first pattern of nano-structures.

6. The microscope slide of claim 2, wherein the disc is characterized by a disc center, the first pattern of nano-structures lying in a first annular zone at a first radial distance from the disc center, and the second pattern of grooves lying in a second annular zone at a second radial distance from the disc center that is different from the first radial distance; and wherein the second pattern of grooves is configured to allow tracking and focusing adjustments to be made during optical interrogation of the fluid sample.

7. The microscope slide of claim 1 wherein the second pattern extends circumferentially over the substrate disc, such that over a small fraction of the top surface, the second pattern of grooves comprises a series of concentric arcuate grooves.

8. The microscope slide of claim 1 wherein the metallic alloy is selected from the group consisting of Sb—Te, In—Sb, SiZ, and NbO2.

9. A method of fabricating a microscope slide; the method comprising:
   creating a first pattern of nano-structures, having dimensions between 0.1 nm and 100 nm, a second pattern of grooves, and a third pattern of ridges into a top surface of a substrate disc;
   creating a fourth pattern of microfluidic features into the substrate disc;
   depositing a metallic alloy with non-linear optical properties onto a first surface of a cover glass; and
   bonding the cover glass to the ridges of the substrate disc to form a sealed chamber between the first surface of the cover glass and the top surface of the substrate disc, such that the ridges determine a height of the sealed chamber.

10. The method of claim 9 wherein the first pattern of nano-structures is configured to interact with a fluid sample such that particles in the sample are contained, guided, and/or otherwise positioned within the chamber to allow for optical interrogation using a microscope.

11. The method of claim 10 wherein the fourth pattern of microfluidic features is configured to guide the fluid sample along a spiral path over the top surface, within the chamber.

12. The method of claim 10 wherein the fourth pattern of microfluidic features is configured to provide entry of the fluid sample into the first pattern of nano-structures from an external source.

13. The method of claim 12, wherein the fourth pattern of microfluidic features is further configured to provide exit of a portion of the fluid sample out of the first pattern of nano-structures.

14. The method of claim 10, wherein the disc is characterized by a disc center, the first pattern of nano-structures lying in a first annular zone at a first radial distance from the disc center, and the second pattern of grooves lying in a second annular zone at a second radial distance from the disc center that is different from the first radial distance; and wherein the second pattern of grooves is configured to allow tracking and focusing adjustments to be made during optical interrogation of the fluid sample.

15. The method of claim 9, wherein the second pattern extends circumferentially over the substrate disc, such that over a small fraction of the top surface, the second pattern of grooves comprises a series of concentric arcuate grooves.

16. The method of claim 9, wherein the metallic alloy is selected from the from the group consisting of Sb—Te, In—Sb, SiZ, and NbO2.

17. The method of claim 9 wherein the metallic alloy is selected such that the extinction coefficient of the alloy, when addressed by a laser beam of an optical read-out system, is sufficiently reduced to create a dynamic pinhole aperture.

18. A method of optical interrogation of a fluid sample present in a chamber within a microscope slide comprising a circular disc bonded to a cover glass; the method comprising:

operating a dual-beam optical pick-up comprising first and second spatially separated beams, the first beam being an imaging beam and the second beam being a track-and-focus beam, such that:

the imaging beam passes through the cover glass to interact with components of the fluid sample present within the chamber in a first annular zone of the microscope slide, ultimately forming one or more images of the components; and the track-and-focus beam passes through the cover glass to interact with a pattern of grooves present within a second annular zone of the microscope slide, radially displaced from the first annular zone, such that signals are provided that enable stabilization of the imaging beam with respect to at least one of raster scanning in a plane parallel to the microscope slide, and focus in a direction perpendicular to the microscope slide.

19. The method of claim 18 wherein the cover glass comprises a metallic alloy with non-linear optical properties, such that when the imaging beam passes through the cover glass a dynamic pinhole aperture is created.

20. The method of claim 18, wherein the optical interrogation is carried out using a modified optical disc player.

* * * * *